US011145056B2

(12) United States Patent
Chan

(10) Patent No.: US 11,145,056 B2
(45) Date of Patent: Oct. 12, 2021

(54) MULTI-VIEW MAMMOGRAM ANALYSIS METHOD, MULTI-VIEW MAMMOGRAM ANALYSIS SYSTEM, AND NON-TRANSITORY COMPUTER-READABLE MEDIUM

(71) Applicant: INSTITUTE FOR INFORMATION INDUSTRY, Taipei (TW)

(72) Inventor: Kai-Hsuan Chan, Taipei (TW)

(73) Assignee: INSTITUTE FOR INFORMATION INDUSTRY, Taipei (TW)

( * ) Notice: Subject to any disclaimer, the term of this patent is extended or adjusted under 35 U.S.C. 154(b) by 64 days.

(21) Appl. No.: 16/662,049

(22) Filed: Oct. 24, 2019

(65) Prior Publication Data

US 2021/0019880 A1      Jan. 21, 2021

(30) Foreign Application Priority Data

Jul. 19, 2019   (TW) .................................. 108125726

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/7485* (2013.01); *A61B 6/502* (2013.01);
(Continued)

(58) Field of Classification Search
CPC combination set(s) only.
See application file for complete search history.

(56) References Cited

U.S. PATENT DOCUMENTS

| 6,553,356 | B1 | 4/2003 | Good et al. |
| 10,140,709 | B2 | 11/2018 | Kisilev et al. |
| 2006/0177125 | A1* | 8/2006 | Chan .................. G06T 7/44 |
| | | | 382/154 |

FOREIGN PATENT DOCUMENTS

| CN | 106446911 A | * | 2/2017 |
| CN | 107730507 A | * | 2/2018 |

(Continued)

OTHER PUBLICATIONS

Machine translation of CN106446911A (Year: 2017).*
(Continued)

*Primary Examiner* — Vu Le
*Assistant Examiner* — Courtney Joan Nelson
(74) *Attorney, Agent, or Firm* — CKC & Partners Co., LLC

(57) ABSTRACT

A multi-view mammogram image analysis method, multi-view mammogram image analysis system and non-transitory computer-readable medium are provided in this disclosure. The multi-view mammogram image analysis method includes the following operations: inputting a plurality of mammogram images; utilizing a symptom identification model to determine whether the mammogram images have an abnormal state, and generating a plurality of heat maps corresponding to the mammogram images; utilizing a false positive filtering model to determine whether the heat maps have a false positive feature, and generating an abnormal probability corresponding to the heat maps; and utilizing a first threshold to determine the abnormal probability, if the abnormal probability is greater than the first threshold, detecting and outputting a lesion position corresponding to the heat maps.

17 Claims, 13 Drawing Sheets

(51) Int. Cl.
    *A61B 6/00*           (2006.01)
    *G06K 9/62*          (2006.01)
    *G06T 7/13*           (2017.01)

(52) U.S. Cl.
    CPC .............. *G06T 7/97* (2017.01); *G06K 9/6267* (2013.01); *G06T 7/13* (2017.01); *G06T 2207/30068* (2013.01); *G06T 2207/30096* (2013.01)

(56) References Cited

FOREIGN PATENT DOCUMENTS

| | | |
|---|---|---|
| CN | 107886514 A | 4/2018 |
| EP | 3480730 A1 | 5/2019 |

OTHER PUBLICATIONS

F. Dehghan and H. Abrishami-Moghaddam, "Comparison of SVM and neural network classifiers in automatic detection of clustered microcalcifications in digitized mammograms," 2008 International Conference on Machine Learning and Cybernetics, Kunming, 2008, pp. 756-761, doi: 10.1109/ICMLC.2008.4620505. (Year: 2008).*
Machine translation of CN-107730507-A (Year: 2018).*
The office action of the corresponding Taiwanese application dated Feb. 18, 2020.

* cited by examiner

MULTI-VIEW MAMMOGRAM ANALYSIS METHOD, MULTI-VIEW MAMMOGRAM ANALYSIS SYSTEM, AND NON-TRANSITORY COMPUTER-READABLE MEDIUM

CROSS-REFERENCE TO RELATED APPLICATION

This application claims priority to Taiwanese Application Serial Number 108125726, filed on Jul. 19, 2019, which is herein incorporated by reference.

BACKGROUND

Field of Invention

The present application relates to an image processing method, image processing system and non-transitory computer-readable medium. More particularly, the present application relates to a multi-view mammogram analysis method, multi-view mammogram analysis system and non-transitory computer-readable medium.

Description of Related Art

The mammography technique mainly uses low-dose X-rays to examine human breasts, which can detect lesions such as masses or calcifications. The mammography technique is more accurate than the palpation method to find the type and location of the lesion in the breast. Therefore, the mammography images play an important role in breast cancer screening.

However, the prior art of mammography techniques are only used to classify and detect for a single image, and this analysis technique is usually causes a higher false positive situation. Therefore, a mammography analysis method for determining whether the mammography image has the lesion and further determining whether the analysis result is mistaken is required.

SUMMARY

An aspect of the disclosure is to provide a multi-view mammogram analysis method. The multi-view mammogram analysis method includes operations of: inputting a plurality of mammogram images; utilizing a symptom identification model to determine whether the plurality of mammogram images have an abnormal state, and generating a plurality of heat maps corresponding to the plurality of mammogram images; utilizing a false positive filtering model to determine whether the plurality of heat maps have a false positive feature, and generating an abnormal probability corresponding to the plurality of heat maps; and utilizing a first threshold to determine the abnormal probability, if the abnormal probability is greater than the first threshold, detecting and outputting a lesion position corresponding to the plurality of heat maps.

Another aspect of the disclosure is to provide a multi-view mammogram analysis system. The multi-view mammogram analysis system includes a storage device and a processor. The processor is electrically connected to the storage device. The storage device is configured to store a plurality of training images and a plurality of mammogram images. The processor includes an abnormal analyzing unit, a false positive analyzing unit, and an abnormal position analyzing unit. The abnormal analyzing unit is configured for utilizing a symptom identification model to determine whether the plurality of mammogram images have an abnormal state, and generating a plurality of heat maps corresponding to the plurality of mammogram images. The false positive analyzing unit is electrically connected to the abnormal analyzing unit, and configured for utilizing a false positive filtering model to determine whether the plurality of heat maps have a false positive feature, and generating an abnormal probability corresponding to the plurality of heat maps. The abnormal position analyzing unit is electrically connected to the false positive analyzing unit, and configured for utilizing a first threshold to determine the abnormal probability, if the abnormal probability is greater than the first threshold, detecting and outputting a lesion position corresponding to the plurality of heat maps.

Another aspect of the disclosure is to provide a non-transitory computer-readable medium including one or more sequences of instructions to be executed by a processor for performing a multi-view mammogram analysis method, wherein the method includes operations of: inputting a plurality of mammogram images; utilizing a symptom identification model to determine whether the plurality of mammogram images have an abnormal state, and generating a plurality of heat maps corresponding to the plurality of mammogram images; utilizing a false positive filtering model to determine whether the plurality of heat maps have a false positive feature, and generating an abnormal probability corresponding to the plurality of heat maps; and utilizing a first threshold to determine the abnormal probability, if the abnormal probability is greater than the first threshold, detecting and outputting a lesion position corresponding to the plurality of heat maps.

Based on aforesaid embodiments, the multi-view mammogram analysis method, multi-view mammogram analysis system and non-transitory computer-readable medium primarily improve the function of classification and detection of single image in the prior art of mammography techniques. This disclosure is capable of utilizing a trained symptom identification model to determine whether the plurality of mammogram images have the abnormal state, and then utilizing the false positive filtering model to determine whether the plurality of heat maps generated by the symptom identification model have the false positive feature. In some embodiments, this disclosure is able to determine automatically the lesion of breast and decrease the probability of the false positive.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

It will be understood that, in the description herein and throughout the claims that follow, when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Moreover, "electrically connect" or "connect" can further refer to the interoperation or interaction between two or more elements.

It will be understood that, in the description herein and throughout the claims that follow, although the terms "first," "second," etc. may be used to describe various elements, these elements should not be limited by these terms. These terms are only used to distinguish one element from another. For example, a first element could be termed a second element, and, similarly, a second element could be termed a first element, without departing from the scope of the embodiments.

It will be understood that, in the description herein and throughout the claims that follow, the terms "comprise" or "comprising," "include" or "including," "have" or "having," "contain" or "containing" and the like used herein are to be understood to be open-ended, i.e., to mean including but not limited to.

It will be understood that, in the description herein and throughout the claims that follow, the phrase "and/or" includes any and all combinations of one or more of the associated listed items.

It will be understood that, in the description herein and throughout the claims that follow, words indicating direction used in the description of the following embodiments, such as "above," "below," "left," "right," "front" and "back," are directions as they relate to the accompanying drawings. Therefore, such words indicating direction are used for illustration and do not limit the present disclosure.

It will be understood that, in the description herein and throughout the claims that follow, unless otherwise defined, all terms (including technical and scientific terms) have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any element in a claim that does not explicitly state "means for" performing a specified function, or "step for" performing a specific function, is not to be interpreted as a "means" or "step" clause as specified in 35 U.S.C. § 112(f). In particular, the use of "step of" in the claims herein is not intended to invoke the provisions of 35 U.S.C. § 112(f).

Figure 1:
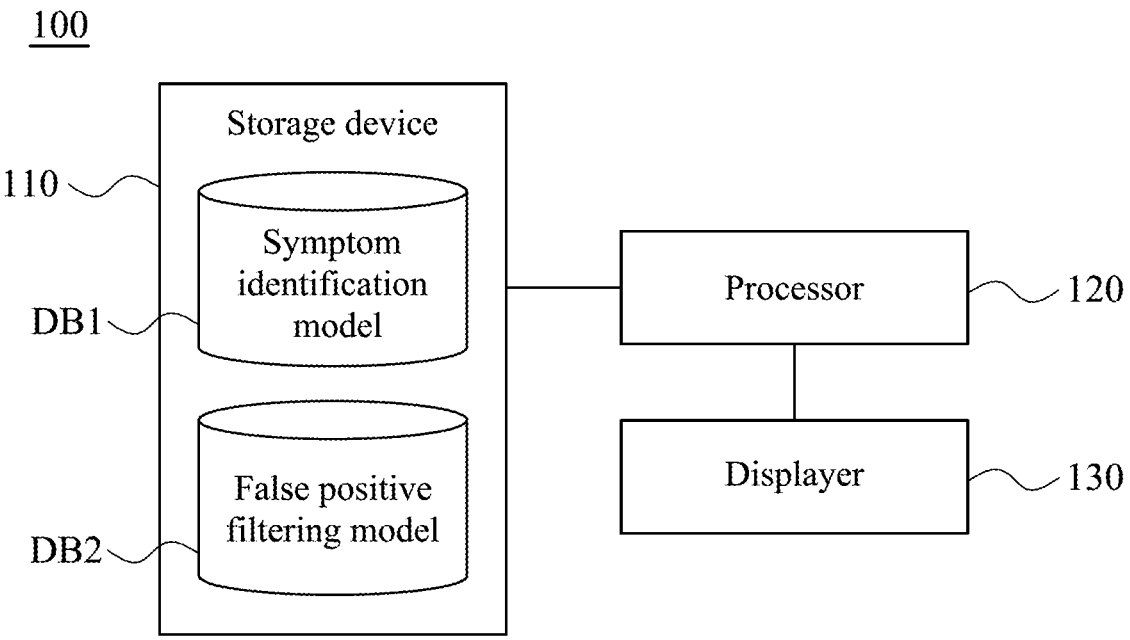
FIG. 1 is a functional block diagram illustrating a multi-view mammogram analysis system according to an embodiment of the disclosure.

Reference is made to FIG. 1, which is a functional block diagram illustrating a multi-view mammogram analysis system 100 according to an embodiment of the disclosure. As shown in FIG. 1, the multi-view mammogram analysis system 100 includes a storage device 110, a processor 120 and a displayer 130. The processor 120 is electrically connected to the storage device 110 and the displayer 130. The storage device 110 is configured to store a plurality of training images, a plurality of mammogram images, a symptom identification model DB1 and a false positive filtering model DB2. In some embodiments, the training images and the mammogram images can be realized to the left mammogram image and the right mammogram image taken at the same time, or the right mammogram images (or the left mammogram images) taken at the different time. The displayer 130 is configured to display the mammogram images after the symptom identification and the false positive analyzing or display the analysis report. The processor 120 is configured to perform the symptom identification and the false positive analyzing for the mammogram images.

In the embodiments of the disclosure, the processor 120 can be implemented by a microcontroller, a microprocessor, a digital signal processor, an application specific integrated circuit, a central processing unit, a control circuit and/or a graphics processing unit. The storage device 110 can be implemented by a memory, a hard disk, a flash drive, a memory card, or etc.

Figure 2:
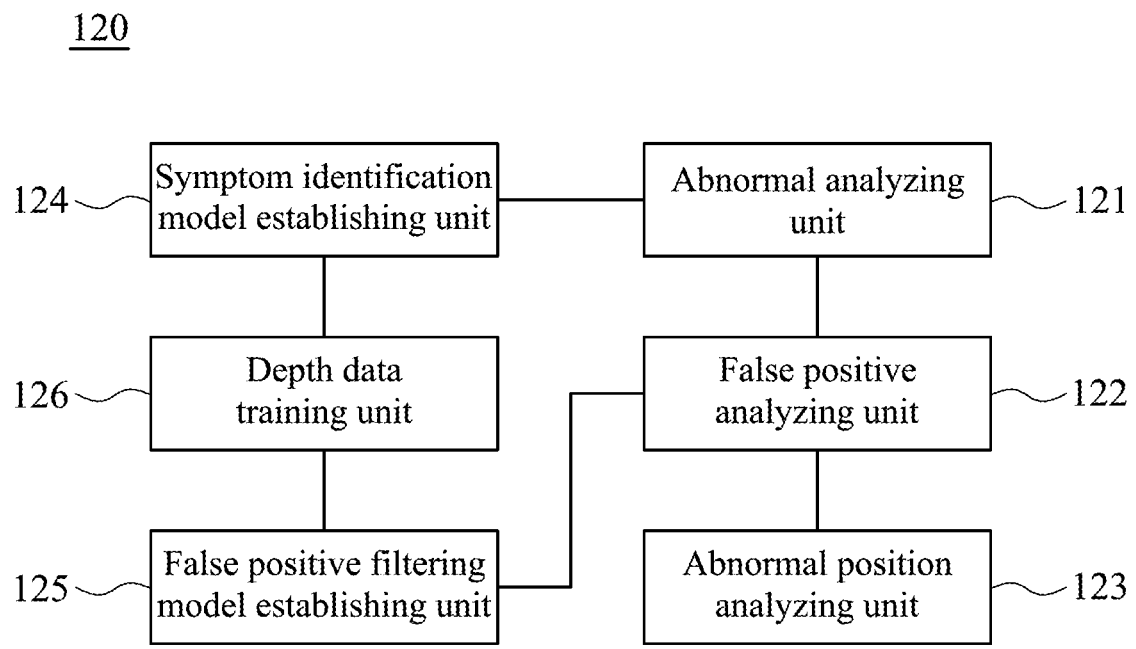
FIG. 2 is a functional block diagram illustrating a processor according to an embodiment of the disclosure.

Reference is made to FIG. 2, which is a functional block diagram illustrating a processor 120 according to an embodiment of the disclosure. As shown in FIG. 2, the processor 120 includes an abnormal analyzing unit 121, a false positive analyzing unit 122, an abnormal position analyzing unit 123, a symptom identification model establishing unit 124, a false positive filtering model establishing unit 125, and a depth data training unit 126. The false positive analyzing unit 122 is electrically connected to the abnormal analyzing unit 121, the abnormal position analyzing unit 123 and the false positive filtering model establishing unit 125. The symptom identification model establishing unit 124 is electrically connected to the abnormal analyzing unit 121 and the depth data training unit 126. The depth data training unit 126 is electrically connected to the symptom identification model establishing unit 124 and the false positive filtering model establishing unit 125.

Figure 3:
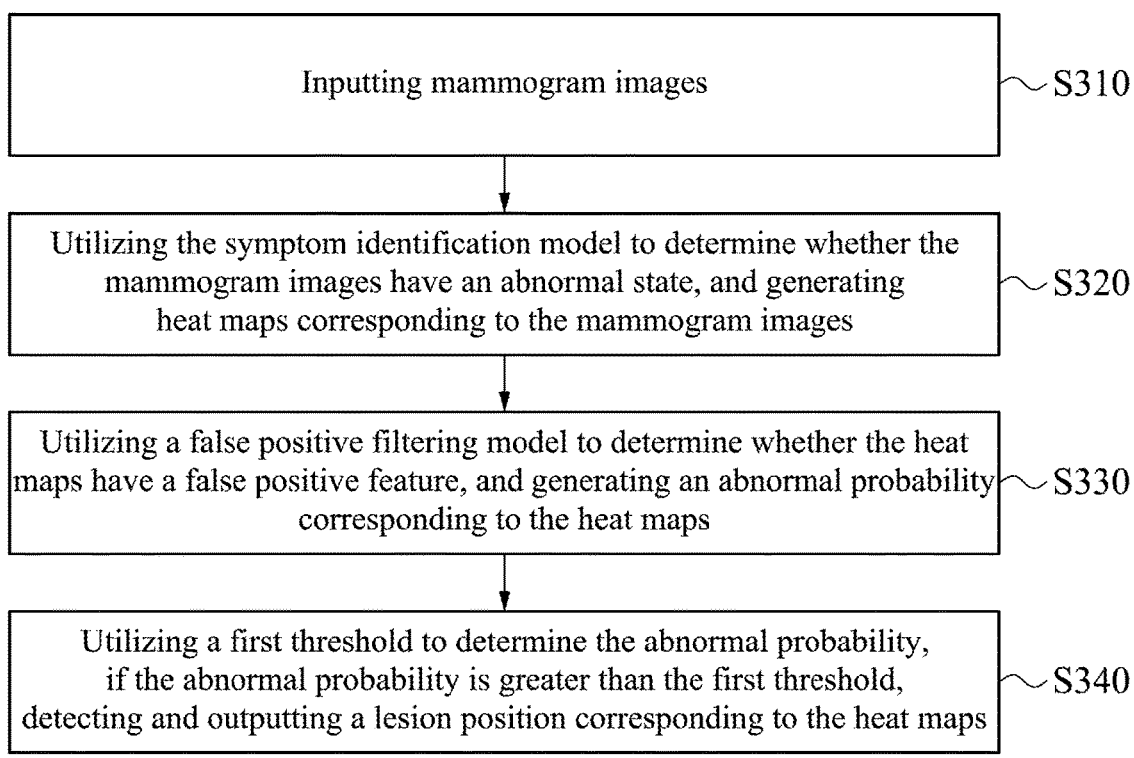
FIG. 3 is a flow diagram illustrating a multi-view mammogram analysis method according to an embodiment of this disclosure.

Reference is made to FIG. 3, which is a flow diagram illustrating a multi-view mammogram analysis method 300 according to an embodiment of this disclosure. In the embodiment, the multi-view mammogram analysis method 300 can be applied to the multi-view mammogram system 100 of FIG. 1. The processor 120 is configured to perform symptom identification and the false positive analyzing for the mammogram images according to the steps described in the following multi-view mammogram analysis method 300.

Afterwards, the multi-view mammogram analysis method 300 firstly executes step S310 inputting mammogram images; and step S320 utilizing the symptom identification model DB1 to determine whether the mammogram images have an abnormal state, and generating heat maps corresponding to the mammogram images. Before executing the step S320, it is necessary to establish the symptom identification model DB1. Firstly, the training image blocks and the labeling results corresponding to the training image blocks are inputted in the symptom identification model DB1. The training image blocks are captured from the training images.

Figure 4B:
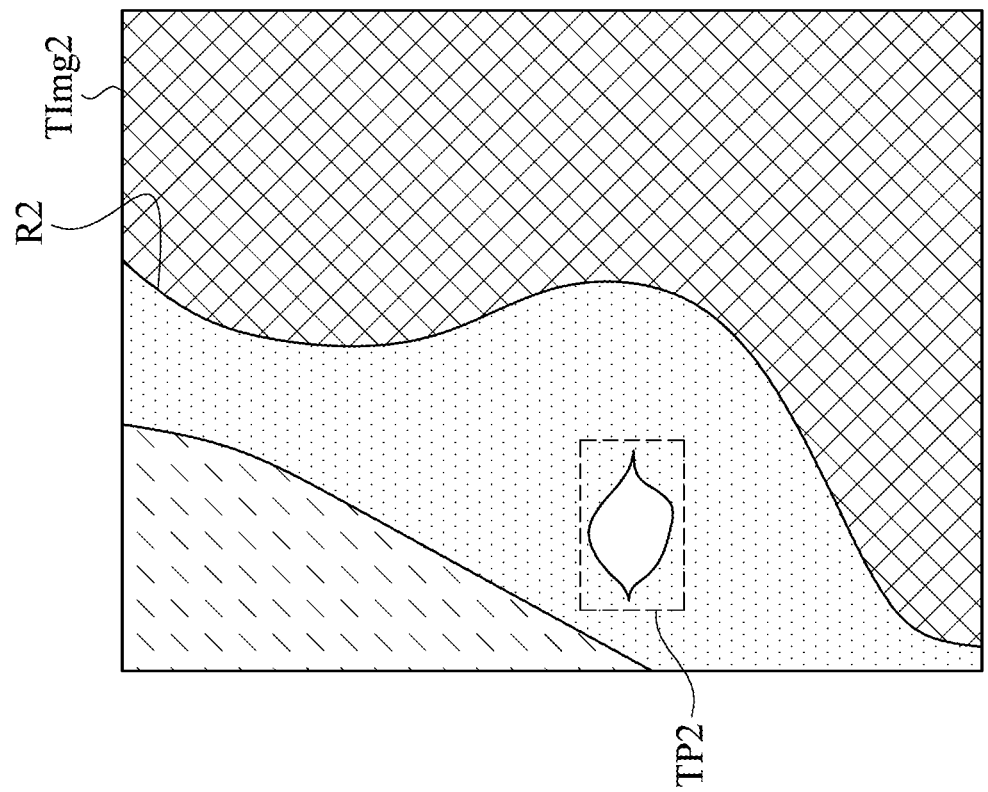
FIG. 4B is a schematic diagram illustrating the training image blocks includes mammary gland and lesion according to an embodiment of this disclosure.
Figure 4A:
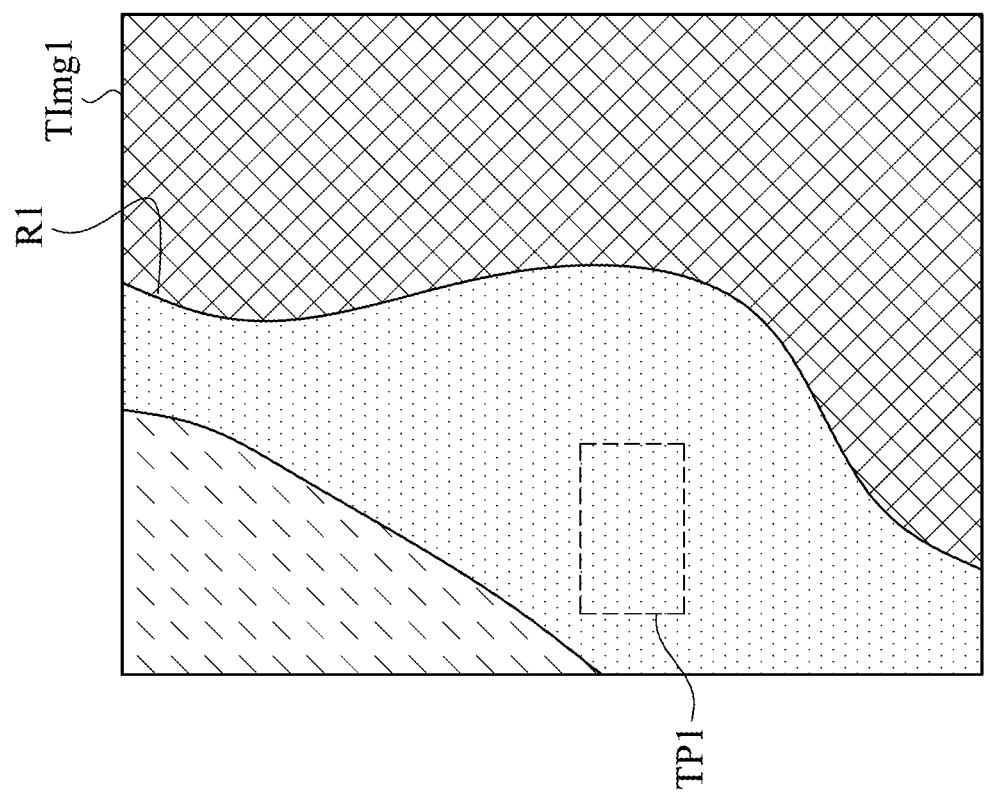
FIG. 4A is a schematic diagram illustrating the training image blocks including the image content of mammary gland according to an embodiment of this disclosure.

Reference is made to FIG. 4A and FIG. 4B. FIG. 4A is a schematic diagram illustrating the training image blocks according to an embodiment of this disclosure, and FIG. 4B is a schematic diagram illustrating the training image blocks according to an embodiment of this disclosure. As shown in FIG. 4A, the symptom identification model establishing unit 124 is configured to capture multiple training image blocks TP1 from the training image TImg1, and each of the training image blocks TP1 has a corresponding labeling result. The breast region R1 includes the mammary gland and the adipose tissue (not shown in figures), and the training image blocks TP1 includes the image content of the normal breast. In other words, the training image blocks TP1 includes the image content of mammary gland and adipose tissue. Thus, the corresponding labeling result of the training image block TP1 is "normal". Only one the training image blocks TP1 is shown in FIG. 4A. In fact, multiple training image blocks TP1 are inputted when training the symptom identification model DB1.

Afterwards, as shown in FIG. 4B, the symptom identification model establishing unit 124 is configured to capture multiple training image blocks TP2 from the training image TImg1, and each of the training image blocks TP2 has a corresponding labeling result. The breast region R2 includes mammary gland, adipose tissue and lesion (not shown in figures). When training the symptom identification model DB1, it will capture the image of the lesion tissue. Thus, the corresponding labeling result of the training image block TP2 is "abnormal". It is noticed that the images of the lesion tissue (masses or calcifications region) are a little part in mammography. If the amount of abnormal image for training is too small, the data augmentation can be performed on the abnormal image. It is utilized the image rotating, the image shifting, the image mirror, etc. to perform the data augmentation.

Afterwards, it is utilized the training image blocks TP1 and TP2, the labeling result corresponding to the training image block TP1 and the labeling result corresponding to the training image block TP2 as the training data, to generate the symptom identification model DB1. It is noticed that the labeling results are marked manual in the training model stage, so that the input training data is more accurate and the identification model can be trained with higher accuracy.

In the embodiment, the aforesaid training data is used to train the convolutional neural network (CNN). After the CNN training passes through the fully connected layers, the training result of the CNN is generated, and then training result is the probability corresponding to the "normal" and "abnormal" of the input image. In the embodiment, the symptom identification model DB1 will generate the heat maps corresponding to the inputted images. Therefore, when the symptom identification model DB1 is trained by the CNN, the global average pooling calculation is removed and only performs the fully connected layers to generate the heat maps corresponding to the inputted images.

Figure 5B:
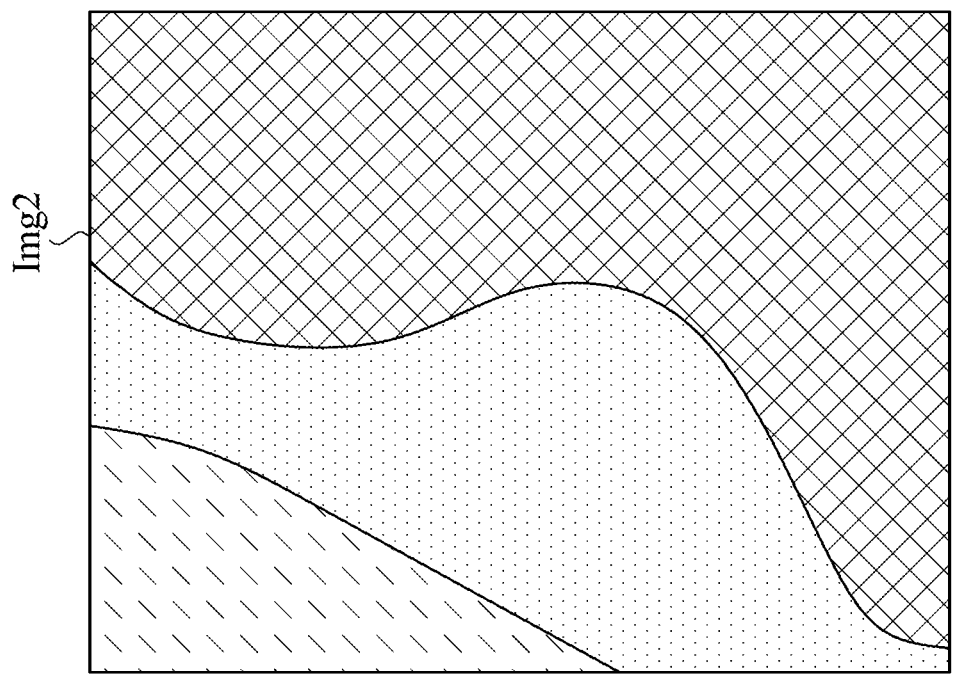
FIG. 5B is a schematic diagram illustrating the mammogram image Img2 according to an embodiment of this disclosure.
Figure 5A:
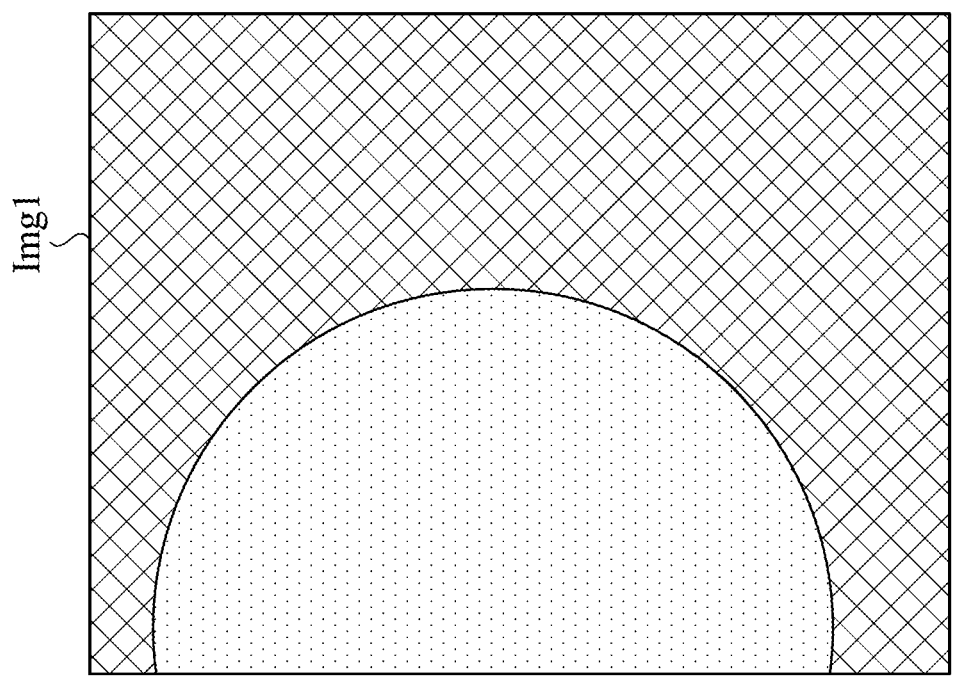
FIG. 5A is a schematic diagram illustrating the mammogram image Img1 according to an embodiment of this disclosure.

The difference between the mammogram images Img1 and Img2 is that the angle of shot is different. The mammogram image Img1 is captured by the craniocaudal (CC) view, and the mammogram image Img2 is captured by the mediolateral oblique (MLO) view. Afterwards, in the step S320, the mammogram images are inputted to the symptom identification model DB1 trained by the CNN, the heat maps corresponding to the inputted images can be generated. Reference is made to FIG. 5A and FIG. 5B. FIG. 5A is a schematic diagram illustrating the mammogram image Img1 according to an embodiment of this disclosure, and FIG. 5B is a schematic diagram illustrating the mammogram image Img2 according to an embodiment of this disclosure. In the embodiment, the mammogram images Img1 and Img2 are inputted to the symptom identification model DB1 to determine whether the mammogram images Img1 and Img2 have an abnormal state, respectively. It is noticed that the mammogram images Img1 and Img2 are the same side of the mammogram image.

It is noticed that the mammogram images include a large part with a black area (represented by a "net" in FIG. 4A and FIG. 4B), and thus before training the training images and inputting the mammogram images to the symptom identification model DB1, pre-processing operations such as image segmentation, brightness correction, etc. are performed. The aforesaid pre-processing operations are a prior art. For the sake of brevity, those descriptions will not be repeated here.

Figure 5D:
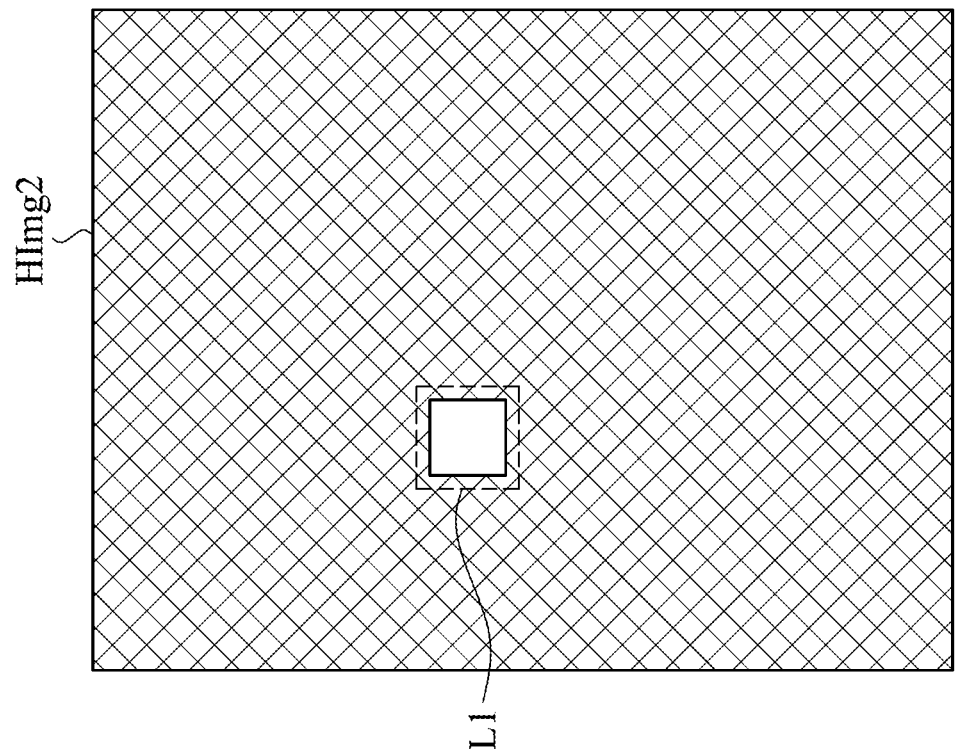
FIG. 5D is a schematic diagram illustrating the heat map corresponding to the mammogram image with an abnormal area according to an embodiment of this disclosure.
Figure 5C:
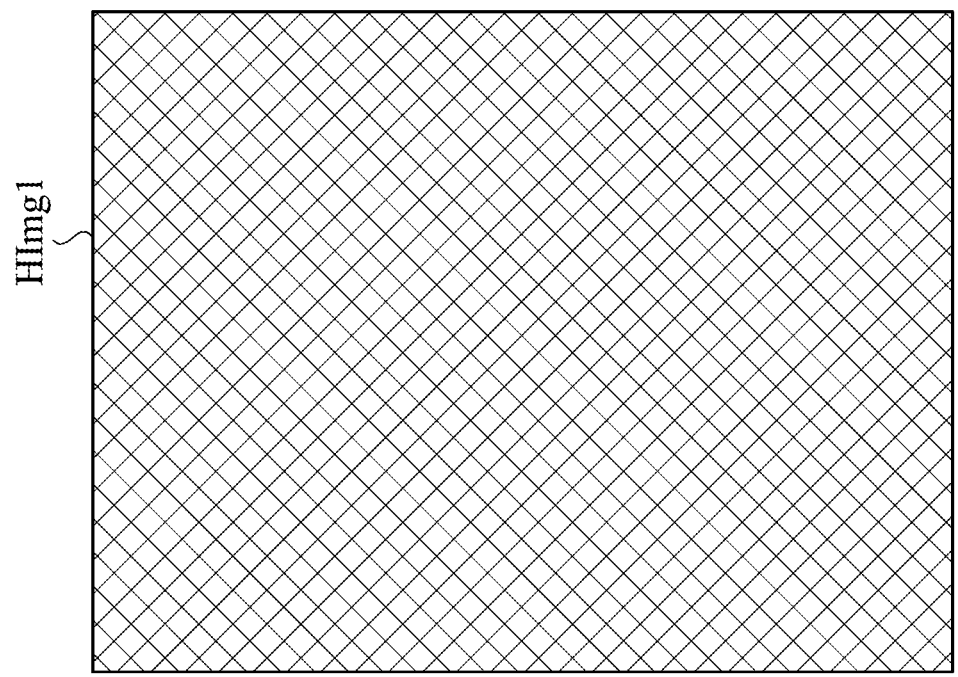
FIG. 5C is a schematic diagram illustrating the heat map corresponding to the normal mammogram image according to an embodiment of this disclosure.

Afterwards, reference is made to FIG. 5C and FIG. 5D. FIG. 5C is a schematic diagram illustrating the heat map HImg1 corresponding to the mammogram image Img1 according to an embodiment of this disclosure, and FIG. 5D is a schematic diagram illustrating the heat map HImg2 corresponding to the mammogram image Img2 according to an embodiment of this disclosure. As shown in FIG. 5C and FIG. 5D, the mammogram image Img1 is processed by the symptom identification model DB1 to generate the heat map HImg1, and the mammogram image Img2 is processed by the symptom identification model DB1 to generate the heat map HImg2. The heat map HImg1 is a black image, indicating that the mammogram image Img1 is a normal mammogram image after being determined by the symptom identification model DB1. The heat map HImg2 has a bright area L1, indicating that the mammogram image Img2 is a mammogram image with an abnormal area after being determined by the symptom identification model DB1.

Figure 6:
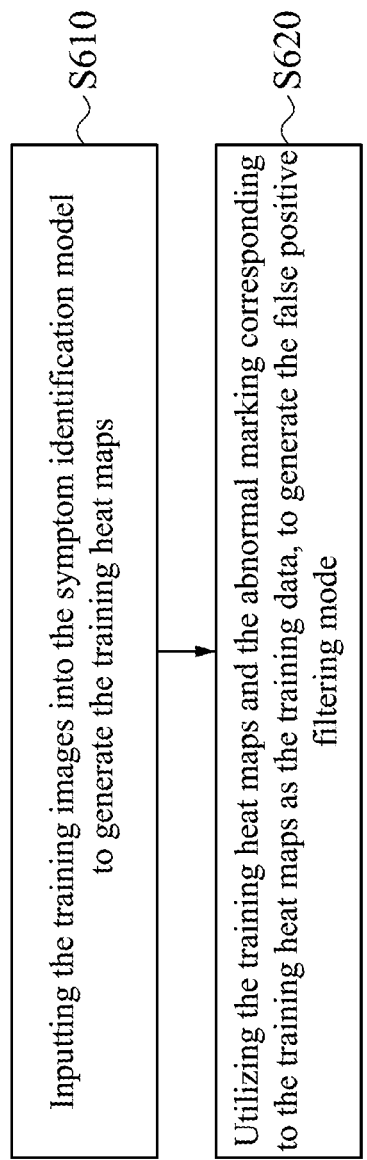
FIG. 6 is a flow diagram illustrating establishing the false positive filtering model according to an embodiment of this disclosure.

Afterwards, the multi-view mammogram analysis method 300 executes step S330 utilizing a false positive filtering model DB2 to determine whether the heat maps have a false positive feature, and generating an abnormal probability corresponding to the heat maps. Before executing step S330, it is necessary to establish the false positive filtering model DB2. Reference is made to FIG. 6, which is a flow diagram illustrating establishing the false positive filtering model DB2 according to an embodiment of this disclosure. As shown in FIG. 6, firstly executes step S610 inputting the training images TImg1 and Timg2 into the symptom identification model to generate the training heat maps HTImg1 and HTimg2.

Figure 7B:
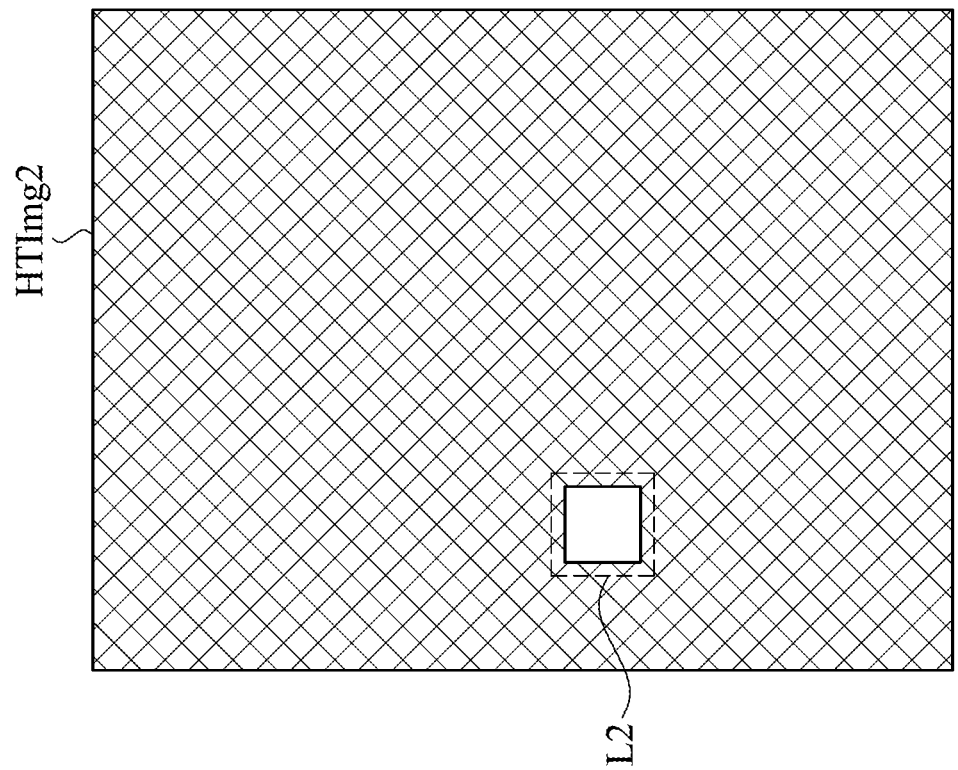
FIG. 7B is a schematic diagram illustrating the heat map corresponding to the training image TImg2 according to an embodiment of this disclosure.
Figure 7A:
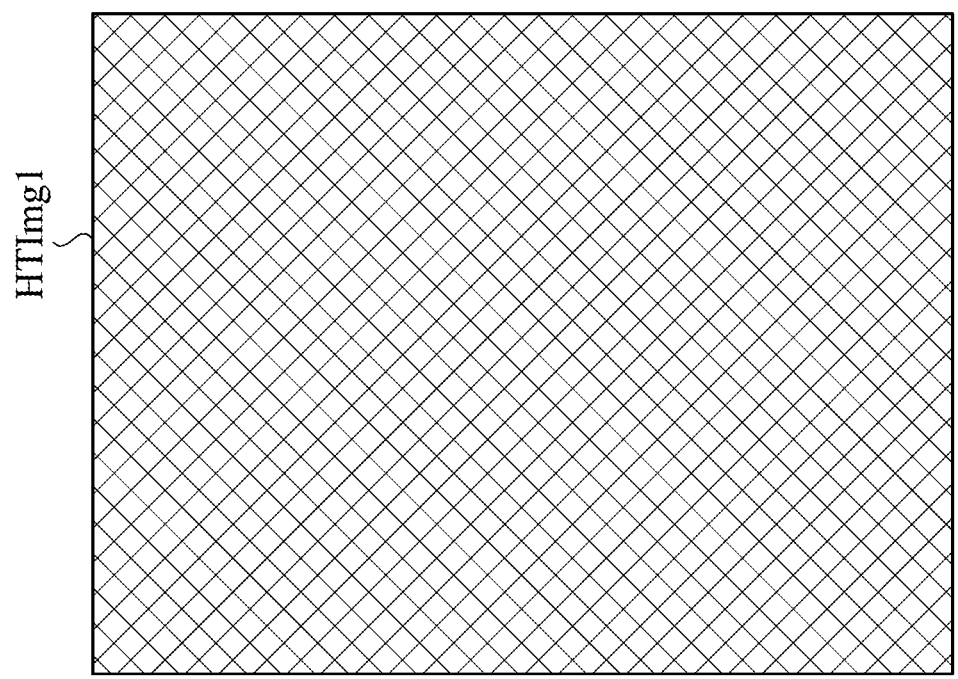
FIG. 7A is a schematic diagram illustrating the heat map corresponding to the training image TImg1 according to an embodiment of this disclosure.

Reference is made to FIG. 7A and FIG. 7B. FIG. 7A is a schematic diagram illustrating the heat map HTImg1 corresponding to the training image TImg1 according to an embodiment of this disclosure, and FIG. 7B is a schematic diagram illustrating the heat map HTImg2 corresponding to the training image TImg2 according to an embodiment of this disclosure. As shown in FIG. 7A, the heat map HTImg1 is a black image, indicating that the training image TImg1 is a normal mammogram image after being determined by the symptom identification model DB1. As shown in FIG. 7B, the heat map HTImg2 has a bright area L2, indicating that training image TImg2 is a mammogram image with abnormal area after being determined by the symptom identification model DB1. Therefore, the heat map HTImg2 has an abnormal marking (the labeling result with abnormal state).

Afterwards, the processor 120 further executes step S620 utilizing the training heat maps HTImg1 and HTImg2 and the abnormal marking corresponding to the training heat maps HTImg1 and HTimg2 as the training data, to generate the false positive filtering model DB2. Based on the aforesaid embodiment, the heat maps HTImg1 and HTImg2 and the abnormal marking corresponding to the heat map HTImg2 are inputted to the CNN to determine the probability corresponding to the "normal" and "abnormal" of the input image. It is noticed that the input images are necessary to execute the convolutional calculation to merge the input images, because the input images are trained at the same time. The input images can be the multiple images of the same side or multiple images of both sides.

Afterwards, if the mammogram image has the abnormal region, the abnormal region is detected form the mammogram image of the CC view and the mammogram image of the MLO view at the same time. However, the processor 120 may mark the mammary gland and the adipose tissue as the abnormal state (masses or calcifications region) due to differences in personal body conditions. In this situation, the mammogram image of the CC view and the mammogram image of the MLO view will not detect the abnormal region at the same time or the positions of the abnormal region are different. Therefore, the situation of misjudgments can be filtered to increase the accuracy of determination through referencing the images with different angels in the training stage.

Afterwards, when the false positive filtering model DB2 is trained, in the step S330, the heat maps HImg1 and Himg2 are inputted to the false positive filtering model DB2 and the false positive filtering model DB2 is utilized to determine whether the heat maps HImg1 and Himg2 have a false positive feature, respectively, and generate an abnormal probability corresponding to the heat maps HImg1 and Himg2, respectively. Afterwards, the multi-view mammogram analysis method 300 executes step S340 utilizing a first threshold to determine the abnormal probability, if the abnormal probability is greater than the first threshold, then detecting and outputting a lesion position corresponding to the heat maps.

In the embodiment, if the abnormal probability is less than the first threshold, it is represented that the range of the abnormal region is smaller, and in other words, it can be realized as the situation of misjudgments (the false positive situation). As the embodiment shown in FIG. 5A to FIG. 5D, the FIG. 5A and the FIG. 5B are the normal mammogram image. However, the FIG. 5B is misjudged as an abnormal mammogram image (the heat map HImg1 includes the bright area L1) in the judgement of the step S320. When performing the false positive determination, the abnormal probability corresponding to the heat map HImg2 is less than the first threshold, and thus the labeling result with abnormal state of the mammogram image (FIG. 5B) is cancelled.

Figure 8:
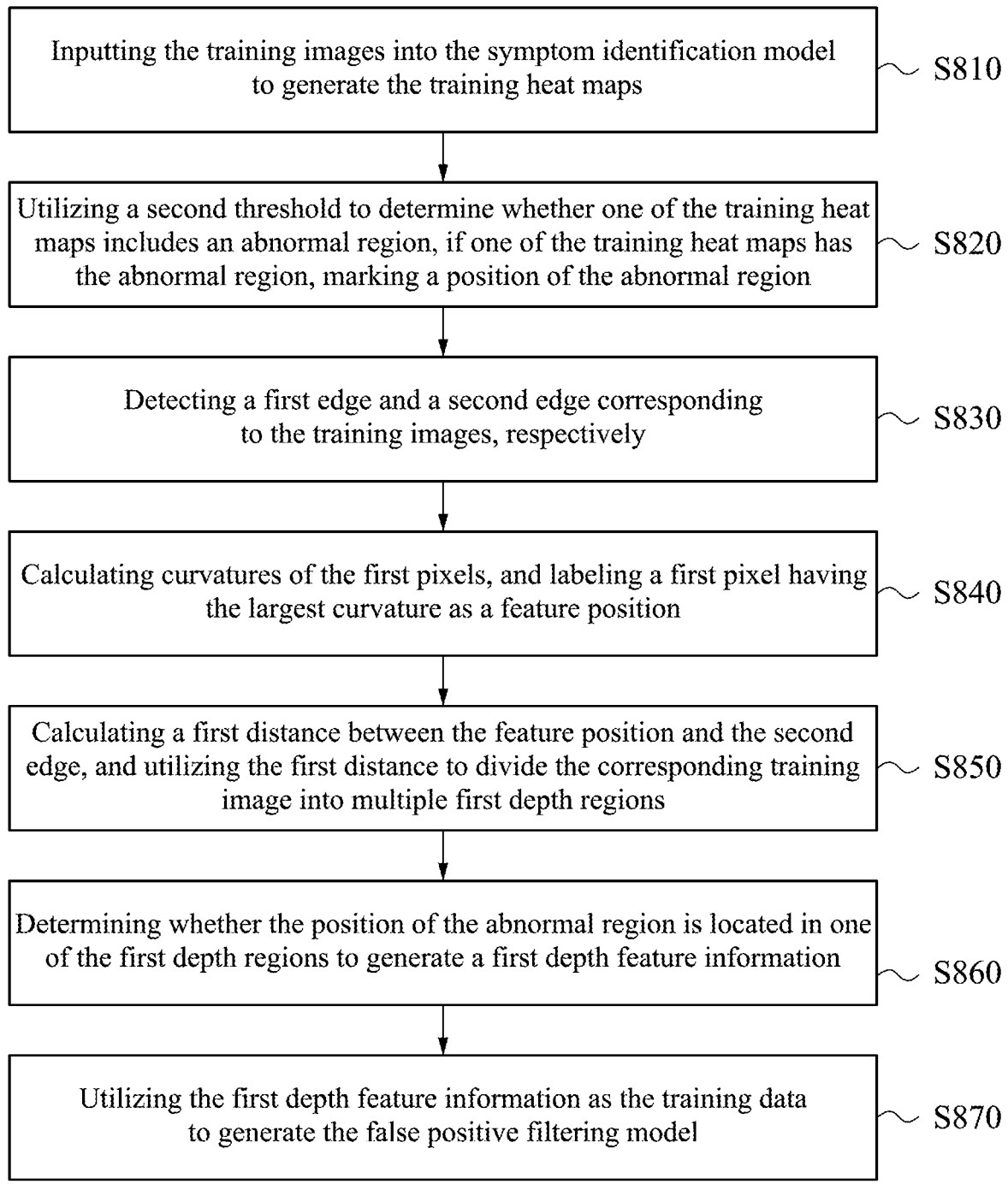
FIG. 8 is a flow diagram illustrating establishing the false positive filtering model according to an embodiment of this disclosure.

In another embodiment, additional depth data can be utilized to train the false positive filtering model DB2, so that the false positive filtering model DB2 can be more accurate. Reference is made to FIG. 8, which is a flow diagram illustrating establishing the false positive filtering model DB2 according to an embodiment of this disclosure. As shown in FIG. 8, the operation of the step S810 is similar with the operation of the step S610. For the sake of brevity; those descriptions will not be repeated here. Afterwards, the processor 120 further executes step S820 utilizing a second threshold to determine whether one of the training heat maps has an abnormal region, if one of the training heat maps has the abnormal region, marking a position of the abnormal region. With respect to the training heat map HTImg2 as shown in FIG. 7B as an example, the bright area L1 with higher gray level, so the second threshold value is used to filter out the area with lower gray level, and thus the center coordinate (hx1, hy1) of the bright area L1 can be calculated.

Figure 9B:
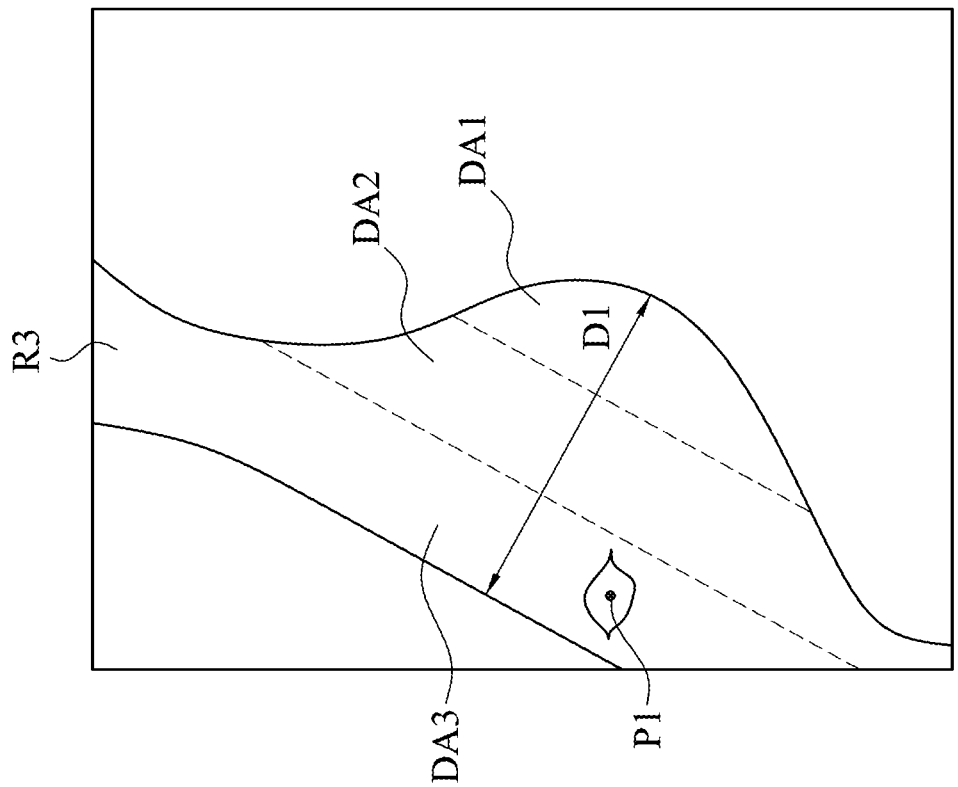
FIG. 9B is a schematic diagram illustrating the depth regions of the training image according to an embodiment of this disclosure.
Figure 9A:
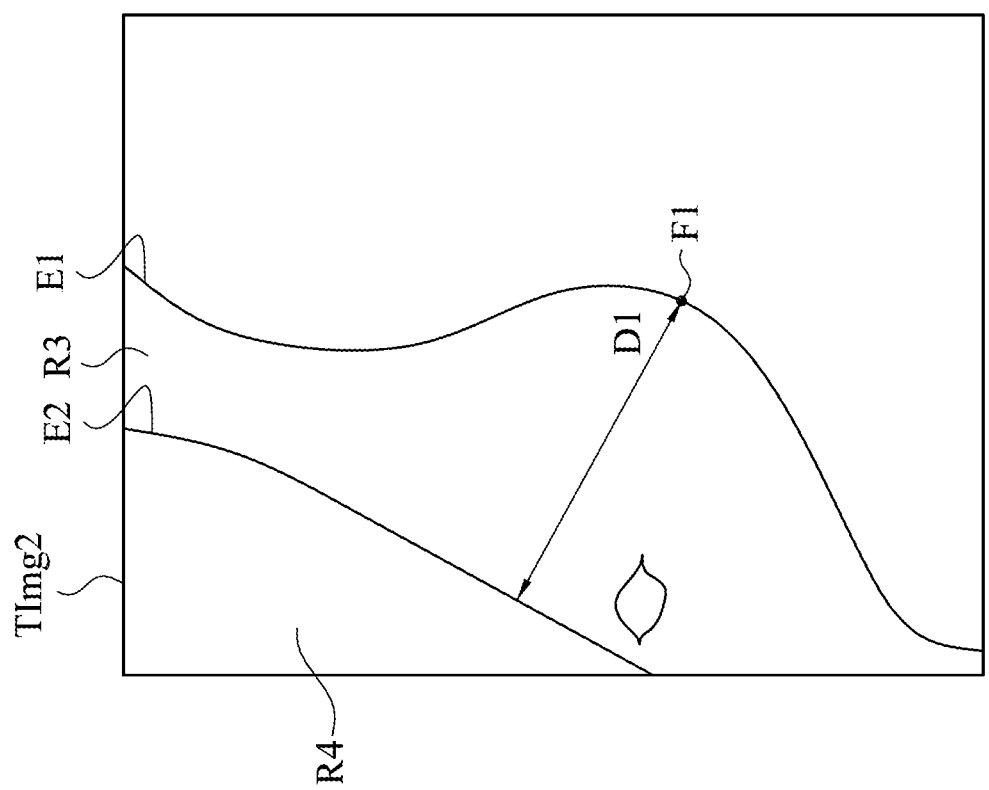
FIG. 9A is a schematic diagram illustrating the edge of the mammogram image corresponding to the training image according to an embodiment of this disclosure.

Afterwards, the processor 120 further executes step S830 detecting a first edge and a second edge corresponding to the training images, respectively. Reference is made to FIG. 9A, which is a schematic diagram illustrating the edge of the mammogram image corresponding to the training image TImg2 according to an embodiment of this disclosure. As shown in FIG. 9A, firstly, the edges of the breast and the pectoralis major muscle are detected. In general case, the mammogram image can be divided into a background area and a breast area, and the background area is usually composed of pixels with lower gray level. Thus, the threshold can be utilized to filter the pixels of the breast area R3. After finding the pixels of the breast area R3, labeling pixels adjacent to the background region in the breast area R3 as pixels of the first edge E1. Afterwards, the pectoralis major muscle area R4 has higher gray level in the mammogram image, the edge detection can be performed on the training image TImg2 to find the second edge E2 (the edge of the pectoralis major muscle).

Afterwards, the processor 120 further executes step S840 calculating curvatures of the first pixels, and labeling a first pixel having the largest curvature as a feature position. Afterwards, it is utilized the curvature formula to calculate the curvatures of the first pixels on the first edge E1. If the curve of first edge E1 undergoes a tight turn, the curvature of the curve is large. Thus, the first pixel having the largest curvature as the feature position F1. In this case, the position with the largest curvature usually is the position of the nipple, and thus the position of the nipple is labeled as the feature position F1. In another embodiment, the threshold is utilized to filter the position with larger curvature, and further to calculate the position of the nipple. However, the disclosure is not limited thereto.

Afterwards, the processor 120 further executes step S850 calculating a first distance between the feature position and the second edge, and utilizing the first distance to divide the corresponding training image TImg2 into multiple first depth regions. As shown in FIG. 9A, after calculating the feature position F1, the vertical distance D1 from the feature position F1 to the second edge E2 can be calculated, and then the breast region R3 is divided into multiple first depth regions according to the length of the distance D1. Reference is made to FIG. 9B, which is a schematic diagram illustrating the depth regions of the training image TImg2 according to an embodiment of this disclosure. As shown in FIG. 9B, multiple first depth regions include a depth region DA1, a depth region DA2 and a depth region DA3. The dividing lines that distinguish the depth region DA1, DA2, and DA3 are perpendicular to the distance D1.

Afterwards, the processor 120 further executes step S860 determining whether the position of the abnormal region is located in one of the first depth regions to generate a first depth feature information. As shown in FIG. 7B and FIG. 9B, the abnormal region is the bright area L1 in the FIG. 7B, and the center coordinate system of the bright area L1 is (hx1, hy1). Thus, the bright area L1 can be mapped to the same position in the FIG. 9B. The position P1 is in the depth region DA3, and the first depth feature information can be represented as the vector form. In this case, the first depth feature information corresponding to the training image TImg2 can be represented as (0, 0, 1), and in other words, there is an abnormal region in the depth region DA3.

Afterwards, the processor 120 further executes step S870 utilizing the first depth feature information as the training data to generate the false positive filtering model DB2. The operation of the step S870 is similar with the operation of the step S630, and the difference between the step S870 and the step S630 is that further input the first depth feature information as the training data. It is noticed that each training images corresponds to a set of depth feature information. When the false positive filtering model is trained, the vector can be cascaded with the corresponding training image and inputted to the fully connected layer at the same time.

It is noticed that in addition to using the first depth feature information as the training data, the auxiliary feature information can also be used as the training data. For example, the patient age can be used as the auxiliary feature information (if the age is higher, the weighting will be higher), and then the auxiliary feature information can be represented as the vector form. The vector can be cascaded with the corresponding training image and inputted to the fully connected layer at the same time. However, the disclosure is not limited thereto.

Figure 10:
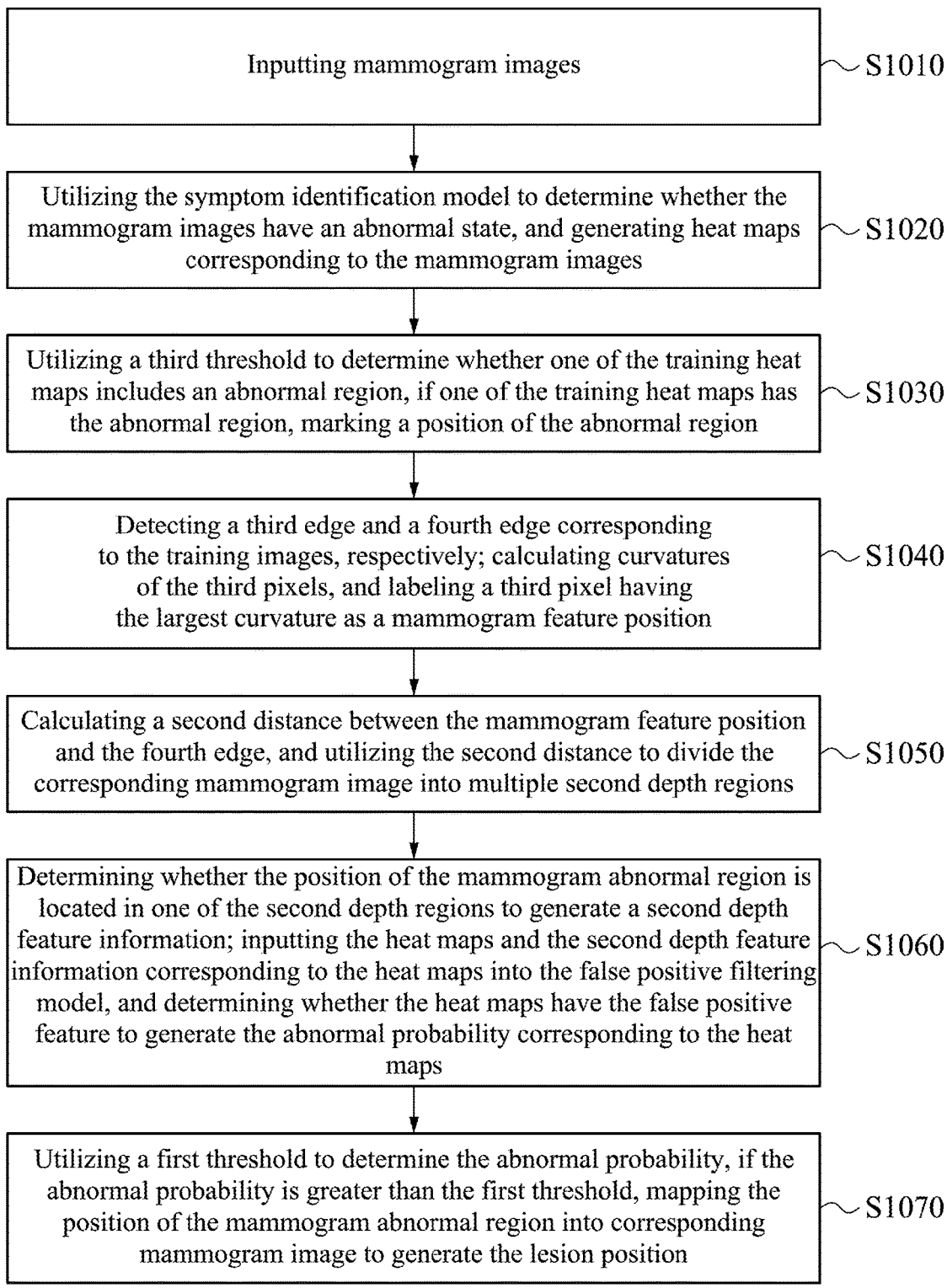
FIG. 10 is a flow diagram illustrating a multi-view mammogram analysis method according to an embodiment of this disclosure.

In the embodiment, when the false positive filtering model DB2 is training, the first depth feature information is used to as the training data, and then the first depth feature information corresponding to the mammogram image also needs to calculate, when the false positive filtering model DB2 is used to determine the false positive feature. Reference is made to FIG. 10, which is a flow diagram illustrating a multi-view mammogram analysis method 1000 according to an embodiment of this disclosure. In the embodiment, the multi-view mammogram analysis method 1000 firstly executes step S1010 inputting mammogram images; and step S1020 utilizing the symptom identification model DB1 to determine whether the mammogram images have an abnormal state, and generating heat maps corresponding to the mammogram images. The operation of the steps S1010 and S1020 are similar with the operation of the steps S310 and S320. For the sake of brevity, those descriptions will not be repeated here.

Figure 11B:
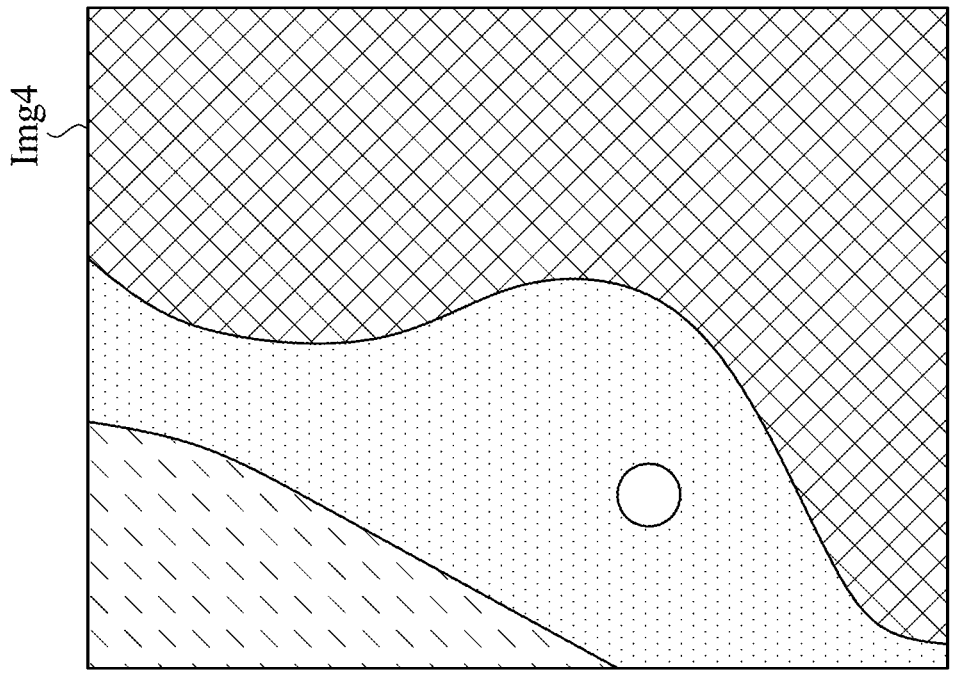
FIG. 11B is a schematic diagram illustrating the mammogram image Img4 according to an embodiment of this disclosure.
Figure 11A:
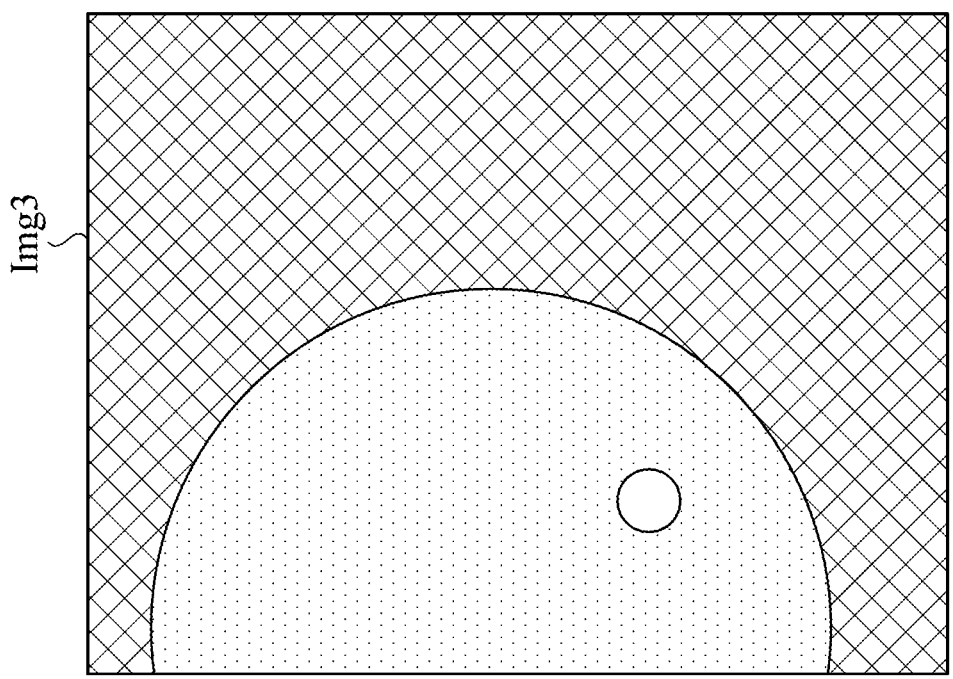
FIG. 11A is a schematic diagram illustrating the mammogram image Img3 according to an embodiment of this disclosure.
Figure 11D:
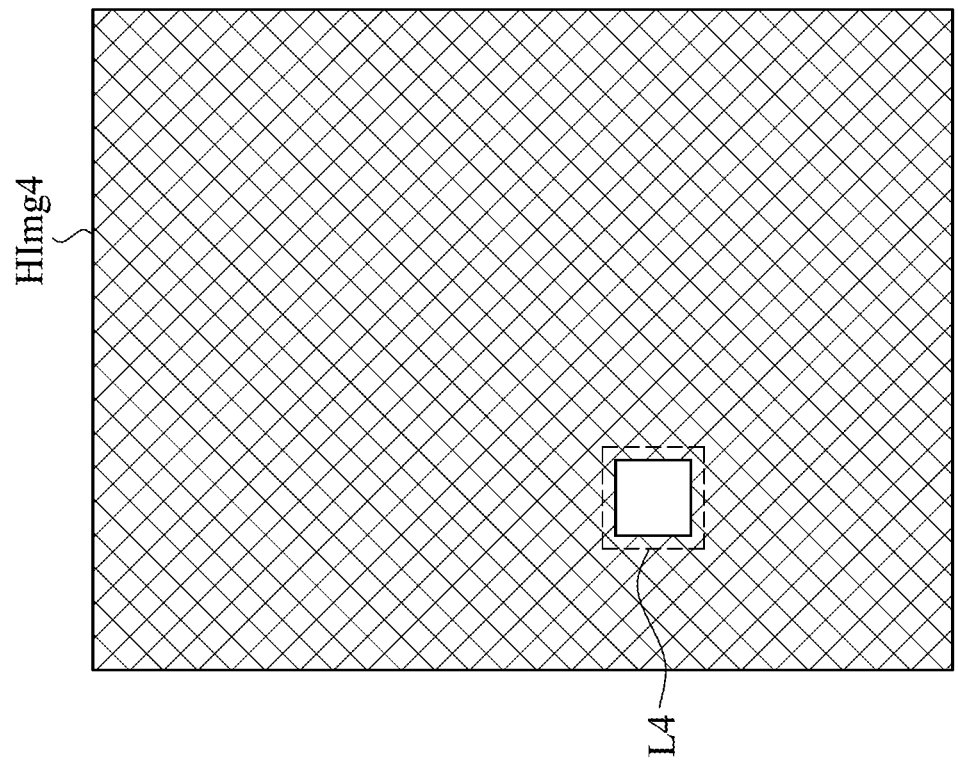
FIG. 11D is a schematic diagram illustrating the heat map HImg4 corresponding to the mammogram image according to an embodiment of this disclosure.
Figure 11C:
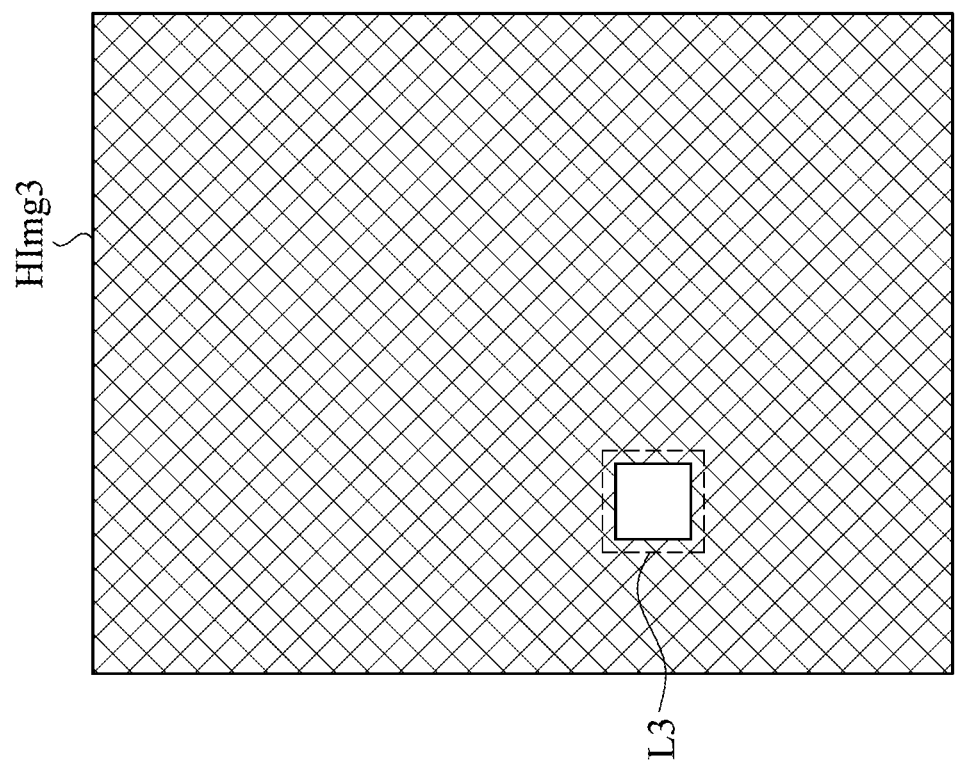
FIG. 11C is a schematic diagram illustrating the heat map HImg3 corresponding to the mammogram image according to an embodiment of this disclosure.

Afterwards, reference is made to FIG. 11A to FIG. 11D. FIG. 11A is a schematic diagram illustrating the mammogram image Img3 according to an embodiment of this disclosure, and FIG. 11B is a schematic diagram illustrating the mammogram image Img4 according to an embodiment of this disclosure. FIG. 11C is a schematic diagram illustrating the heat map HImg3 corresponding to the mammogram image Img3 according to an embodiment of this disclosure, and FIG. 11D is a schematic diagram illustrating the heat map HImg4 corresponding to the mammogram image Img4 according to an embodiment of this disclosure. The mammogram images Img3 and Img4 are inputted to the symptom identification model DB1 to determine whether the mammogram images Img3 and Img4 have the abnormal state, respectively. Then, the symptom identification model DB1 will generate the heat maps HImg3 and HImg4 corresponding to the mammogram images Img3 and Img4, respectively.

As shown in FIG. 11C and FIG. 11D, the heat map HImg3 has a bright area L3, indicating that the mammogram image Img3 is a mammogram image with abnormal area after being determined by the symptom identification model DB1. The heat map HImg4 has a bright area L4, indicating that the mammogram image Img4 is a mammogram image with abnormal area after being determined by the symptom identification model DB1.

Afterwards, the multi-view mammogram analysis method 1000 executes step S1030 utilizing a third threshold to determine whether one of the training heat maps HImg3 and HImg4 has an abnormal region, if one of the training heat maps has the abnormal region, marking a position of the abnormal region. In the embodiment, the operation of the step S1030 is similar with the operation of the step S820. For the sake of brevity, those descriptions will not be repeated here. Based on the third threshold, the center coordinate (hx2, hy2) of the bright area L3 and the center coordinate (hx3, hy3) of the bright area L4 can be calculated.

Afterward, the multi-view mammogram analysis method 1000 executes step S1040 detecting a third edge and a fourth edge corresponding to the training images, respectively; calculating curvatures of the third pixels, and labeling a third pixel having the largest curvature as a mammogram feature position. In the embodiment, the operation of the step S1040 is similar with the operation of the steps S830 and S840. For the sake of brevity, those descriptions will not be repeated here.

Figure 12B:
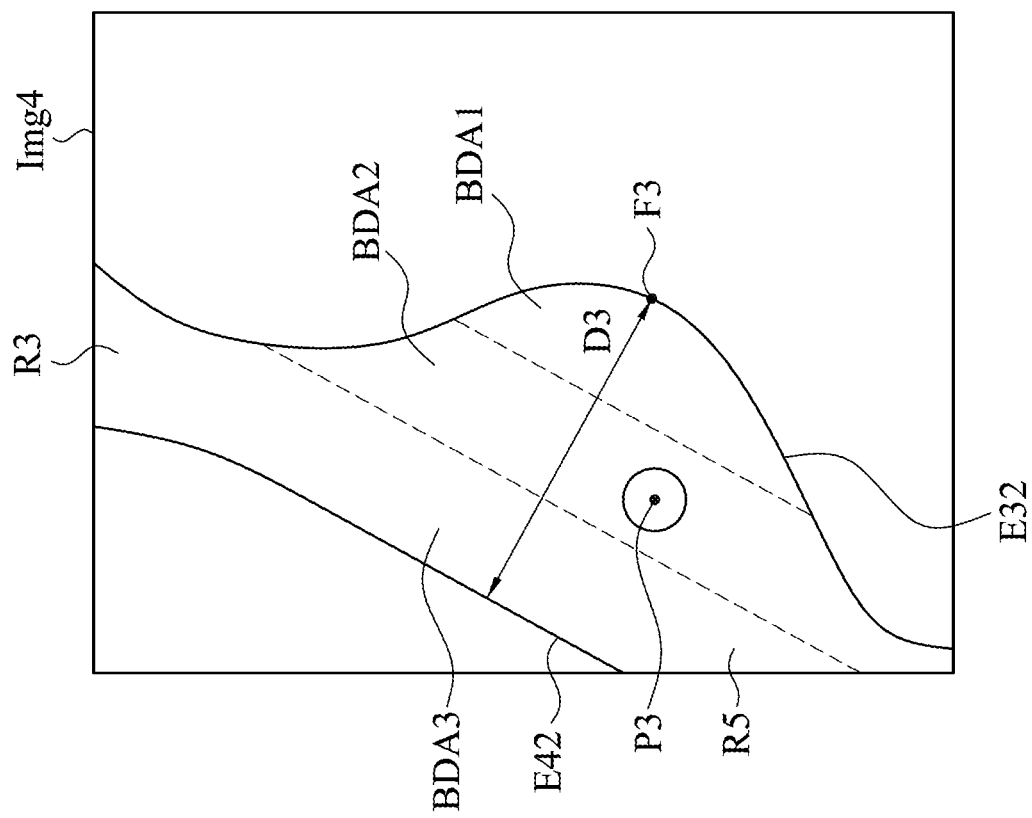
FIG. 12B is a schematic diagram illustrating the edge of the mammogram image Img4 according to an embodiment of this disclosure.
Figure 12A:
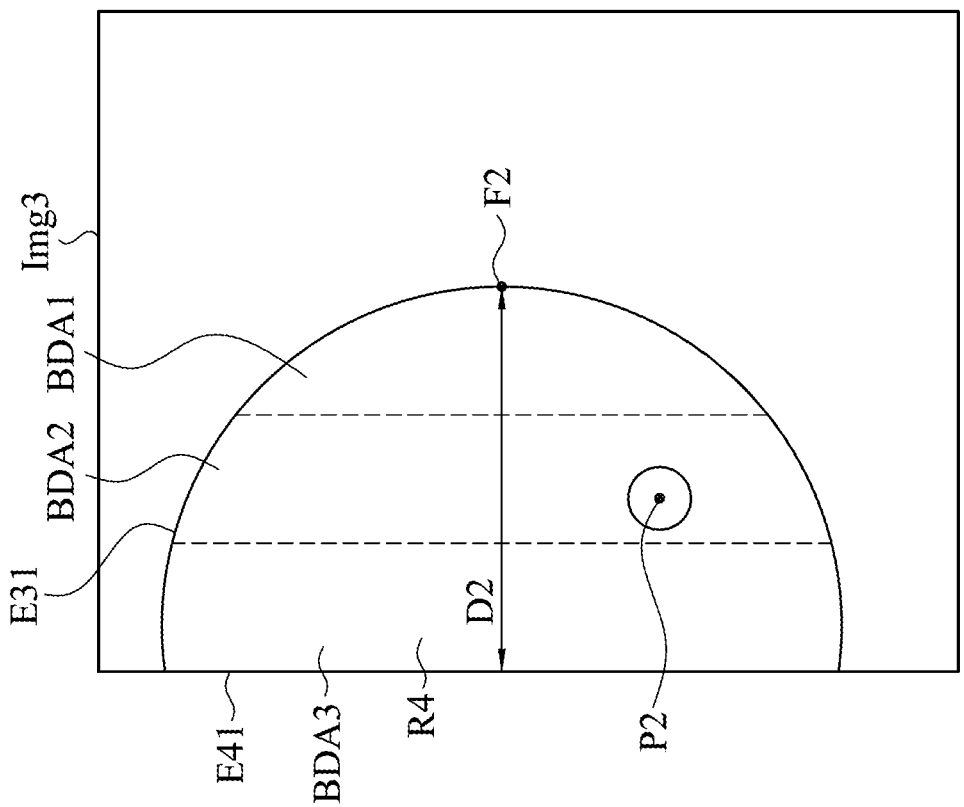
FIG. 12A is a schematic diagram illustrating the edge of the mammogram image Img3 according to an embodiment of this disclosure.

Reference is made to FIG. 12A, which is a schematic diagram illustrating the edge of the mammogram image Img3 according to an embodiment of this disclosure. As shown in FIG. 12A, the edge of the breast area of the mammogram image Img3 is labeled as the third edge E31. The mammogram image Img3 is captured by the CC view as shown in FIG. 12A, and thus this type of image dose not include the region of the pectoralis major muscle. Accordingly, the edge of the mammogram image is labeled as the fourth edge E41. Afterwards, it is utilized the curvature formula to calculate the curvatures of the third pixels on the third edge E31, and find the third pixel having the largest curvature as the mammogram feature position F2.

Reference is made to FIG. 12B, which is a schematic diagram illustrating the edge of the mammogram image Img4 according to an embodiment of this disclosure. Based on aforesaid embodiment, as shown in FIG. 12B, it is labeled the third edge E32 (the edge of the breast area) and the fourth edge E42 (the edge of the pectoralis major muscle) in the mammogram image Img4. Then, it is utilized the curvature formula to calculate the curvatures of the third pixels on the third edge E32, and find the third pixel having the largest curvature as the mammogram feature position F3.

Afterward, the multi-view mammogram analysis method 1000 executes step S1050 calculating a second distance between the mammogram feature position and the fourth edge, and utilizing the second distance to divide the corresponding mammogram image into multiple second depth regions. In the embodiment, the operation of the step S1050 is similar with the operation of the step S850. For the sake of brevity, those descriptions will not be repeated here. As shown in FIG. 12A, after calculating the mammogram feature position F2, the vertical distance D2 from the mammogram feature position F2 to the third edge E41 can be calculated, and then the breast region R4 is divided into multiple depth regions BDA1, BDA2, and BDA3 according to the length of the distance D2. The dividing lines that distinguish the depth region BDA1, BDA2, and BDA3 are perpendicular to the distance D2.

Afterwards, similarly, as shown in FIG. 12B, after calculating the mammogram feature position F3, the vertical distance D3 from the mammogram feature position F3 to the third edge E42 can be calculated, and then the breast region R5 is divided into multiple depth regions BDA1, BDA2, and BDA3 according to the length of the distance D3. The dividing lines that distinguish the depth region BDA1, BDA2, and BDA3 are perpendicular to the distance D3.

Afterwards, the multi-view mammogram analysis method 1000 executes step S1060 determining whether the position of the mammogram abnormal region is located in one of the second depth regions to generate a second depth feature information; inputting the heat maps and the second depth feature information corresponding to the heat maps into the false positive filtering model, and determining whether the heat maps have the false positive feature to generate the abnormal probability corresponding to the heat maps. In the embodiment, the operation of the step S1060 is similar with the operation of the steps S860 and S870. For the sake of brevity, those descriptions will not be repeated here. As shown in FIG. 11C and FIG. 12A, the abnormal area as shown in FIG. 11C is the bright area L3, and the center coordinate (hx2, hy2) of the bright area L3. Thus, the bright area L3 can be mapped to the same position P2 in the FIG. 12A, and the position P2 is in the depth region BDA2. In this case, the second depth feature information corresponding to the mammogram image Img3 can be represented as (0, 1, 0), and in other words, there is an abnormal region in the depth region BDA2.

Afterwards, similarly, as shown in FIG. 11D and FIG. 12B, the abnormal area as shown in FIG. 11D is the bright area L4, and the center coordinate (hx3, hy3) of the bright area L4. Thus, the bright area L4 can be mapped to the same position P3 in the FIG. 12B, and the position P3 is in the depth region BDA2. In this case, the second depth feature information corresponding to the mammogram image Img4 can be represented as (0, 1, 0), and in other words, there is an abnormal region in the depth region BDA2. Afterwards, the second depth feature information (0, 1, 0) corresponding to the mammogram image Img3 is concatenated with the second depth feature information (0, 1, 0) corresponding to the mammogram image Img4 to generate the vector (0, 1, 0, 0, 1, 0).

Afterwards, the heat maps HImg3 and HImg4 the second depth feature information corresponding to the heat maps HImg3 and HImg4 are inputted to the false positive filtering model DB2 to determine whether the heat maps HImg3 and HImg4 have the false positive feature and generate the abnormal probability corresponding to the heat maps HImg3 and HImg4. The multi-view mammogram analysis method 1000 executes step S1070 utilizing a first threshold to determine the abnormal probability, if the abnormal probability is greater than the first threshold, mapping the position (P2 and P3) of the mammogram abnormal region (the bright areas L3 and L4) into corresponding mammogram image to generate the lesion position.

Afterwards, in the embodiment shown in FIG. 11A and FIG. 11B, after the determination of step S1020 is performed, the mammogram images of the FIG. 11A and FIG. 11B are determined as the abnormal mammogram images. When performing the false positive determination, the abnormal probability corresponding to the heat maps HImg3 and HImg4 are greater than the first threshold. Thus, the position of the mammogram abnormal regions (the bright areas L3 and L4) calculated by the step S1030 are mapped into the corresponding mammogram images Img3 and Img4 to generate the lesion position, respectively.

Based on aforesaid embodiments, the multi-view mammogram analysis method, multi-view mammogram analysis system and non-transitory computer-readable medium primarily improve the function of classification and detection of a single image in the prior art of mammography techniques. This disclosure is capable of utilizing trained symptom identification model to determine whether the plurality of mammogram images have the abnormal state, and utilizing the false positive filtering model to determine whether the plurality of heat maps generated by the symptom identification model have the false positive feature. In some embodiments, this disclosure is able to automatically determine the lesion of breast and decrease the probability of the false positive.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A multi-view mammogram analysis method, comprising:
   inputting a plurality of mammogram images, wherein the plurality of mammogram images at least include two mammogram images captured by a craniocaudal view and a mediolateral oblique view from the same side;
   utilizing a symptom identification model to determine whether the plurality of mammogram images have an abnormal state, and generating a plurality of heat maps corresponding to the plurality of mammogram images;
   utilizing a false positive filtering model to determine whether the plurality of heat maps have a false positive feature, and generating an abnormal probability corresponding to the plurality of heat maps, wherein the false positive filtering model is trained by a plurality of training images captured by the craniocaudal view and the mediolateral oblique view; and utilizing a first threshold to determine the abnormal probability, if the abnormal probability is greater than the first threshold, detecting and outputting a lesion position corresponding to the plurality of heat maps.

2. The multi-view mammogram analysis method of claim 1, further comprising:

inputting a plurality of training image blocks, wherein the plurality of training image blocks are captured from a plurality of training images, and the plurality of training image blocks are corresponding to a labeling result, respectively; and utilizing the plurality of training image blocks and the labeling result corresponding to the plurality of training image blocks as a training data, to generate the symptom identification model.

3. The multi-view mammogram analysis method of claim 2, further comprising:

inputting the plurality of training images into the symptom identification model to generate a plurality of training heat maps, wherein the plurality of training heat maps have an abnormal marking; and utilizing the plurality of training heat maps and the abnormal marking corresponding to the plurality of training heat maps as the training data, to generate the false positive filtering model.

4. The multi-view mammogram analysis method of claim 3, further comprising:

utilizing a second threshold to determine whether one of the plurality of training heat maps has an abnormal region, if one of the plurality of training heat maps has the abnormal region, marking a position of the abnormal region.

5. The multi-view mammogram analysis method of claim 4, further comprising:

detecting a first edge and a second edge corresponding to the plurality of training images, respectively, wherein the first edge comprises a plurality of first pixels;

calculating curvatures of the plurality of first pixels, and labeling a first pixels having a largest curvature as a feature position;

calculating a first distance between the feature position and the second edge, and utilizing the first distance to divide the corresponding training image into a plurality of first depth regions;

determining whether the position of the abnormal region is located in one of the plurality of first depth regions to generate a first depth feature information; and utilizing the first depth feature information as the training data to generate the false positive filtering model.

6. The multi-view mammogram analysis method of claim 1, wherein detecting and outputting the lesion position corresponding to the plurality of heat maps, further comprising:

utilizing a third threshold to determine whether one of the plurality of heat maps has a mammogram abnormal region, if one of the plurality of heat maps has the mammogram abnormal region, marking a position of the mammogram abnormal region.

7. The multi-view mammogram analysis method of claim 6, wherein mapping the position of the mammogram abnormal region into the corresponding mammogram image to generate the lesion position.

8. The multi-view mammogram analysis method of claim 6, further comprising:

detecting a third edge and a fourth edge corresponding to the plurality of mammogram images, respectively, wherein the third edge comprises a plurality of third pixels;

calculating curvatures of the plurality of third pixels, and labeling a third pixels having the largest curvature as a mammogram feature position;

calculating a second distance between the mammogram feature position and the fourth edge, and utilizing the second distance to divide the corresponding mammogram image into a plurality of second depth regions;

determining whether the position of the mammogram abnormal region is located in one of the plurality of second depth regions to generate a second depth feature information; and inputting the plurality of heat maps and the second depth feature information corresponding to the plurality of heat maps into the false positive filtering model, and determining whether the plurality of heat maps have the false positive feature to generate the abnormal probability corresponding to the plurality of heat maps.

9. A multi-view mammogram analysis system, comprising:

a storage device, configured for storing a plurality of training images and a plurality of mammogram images, wherein the plurality of mammogram images at least include two mammogram images captured by a craniocaudal view and a mediolateral oblique view from the same side; and a processor, electrically connected to the storage device, the processor comprises:

an abnormal analyzing circuit which is configured for utilizing a symptom identification model to determine whether the plurality of mammogram images have an abnormal state, and generating a plurality of heat maps corresponding to the plurality of mammogram images;

a false positive analyzing circuit which is electrically connected to the abnormal analyzing circuit, and configured for utilizing a false positive filtering model to determine whether the plurality of heat maps have a false positive feature, and generating an abnormal probability corresponding to the plurality of heat maps, wherein the false positive filtering model is trained by a plurality of training images captured by the craniocaudal view and the mediolateral oblique view; and an abnormal position analyzing circuit which is electrically connected to the false positive analyzing circuit, and configured for utilizing a first threshold to determine the abnormal probability, if the abnormal probability is greater than the first threshold, detecting and outputting a lesion position corresponding to the plurality of heat maps.

10. The multi-view mammogram analysis system of claim 9, wherein the processor further comprises:

a symptom identification model establishing circuit which is electrically connected to the abnormal analyzing circuit, and configured for inputting a plurality of training image blocks, wherein the plurality of training image blocks are captured from the plurality of training images, and the plurality of training image blocks are corresponding to a labeling result, respectively; and utilizing the plurality of training image blocks and the labeling result corresponding to the plurality of training image blocks as a training data, to generate the symptom identification model.

11. The multi-view mammogram analysis system of claim 10, wherein the processor further comprises:
a false positive filtering model establishing circuit which is electrically connected to the symptom identification model establishing circuit and the false positive analyzing circuit, and configured for inputting the plurality of training images into the symptom identification model to generate a plurality of training heat maps, wherein the plurality of training heat maps have an abnormal marking; and utilizing the plurality of training heat maps and the abnormal marking corresponding to the plurality of training heat maps as the training data, to generate the false positive filtering model.

12. The multi-view mammogram analysis system of claim 11, wherein the false positive filtering model establishing circuit is further configured for utilizing a second threshold to determine whether one of the plurality of training heat maps has an abnormal region, if one of the plurality of training heat maps has the abnormal region, marking a position of the abnormal region.

13. The multi-view mammogram analysis system of claim 12, wherein the processor further comprises:
a depth data training circuit which is electrically connected to the symptom identification model establishing circuit and the false positive analyzing circuit, and configured for detecting a first edge and a second edge corresponding to the plurality of training images, respectively, wherein the first edge comprises a plurality of first pixel; calculating curvatures of the plurality of first pixels, and labeling a first pixels having a largest curvature as a feature position; calculating a first distance between the feature position and the second edge, and utilizing the first distance to divide the corresponding training image into a plurality of first depth region; determining whether the position of the abnormal region is located in one of the plurality of first depth region to generate a first depth feature information; and utilizing the first depth feature information as the training data to generate the false positive filtering model.

14. The multi-view mammogram analysis system of claim 9, wherein the abnormal position analyzing circuit is further configured for utilizing a third threshold to determine whether one of the plurality of heat maps has a mammogram abnormal region, if one of the plurality of heat maps has the mammogram abnormal region, marking a position of the mammogram abnormal region.

15. The multi-view mammogram analysis system of claim 14, wherein the abnormal position analyzing circuit is further configured for mapping the position of the mammogram abnormal region into the corresponding mammogram image to generate the lesion position.

16. The multi-view mammogram analysis system of claim 14, wherein the abnormal position analyzing circuit is further configured for detecting a third edge and a fourth edge corresponding to the plurality of mammogram images, respectively, wherein the third edge comprises a plurality of third pixels; calculating curvatures of the plurality of third pixels, and labeling a third pixels having the largest curvature as a mammogram feature position; calculating a second distance between the mammogram feature position and the fourth edge, and utilizing the second distance to divide the corresponding mammogram image into a plurality of second depth regions; determining whether the position of the mammogram abnormal region is located in one of the plurality of second depth regions to generate a second depth feature information; and inputting the plurality of heat maps and the second depth feature information corresponding to the plurality of heat maps into the false positive filtering model, and determining whether the plurality of heat maps have the false positive feature to generate the abnormal probability corresponding to the plurality of heat maps.

17. A non-transitory computer-readable medium including one or more sequences of instructions to be executed by a processor for performing a multi-view mammogram analysis method, wherein the method comprises:
inputting a plurality of mammogram images, wherein the plurality of mammogram images at least include two mammogram images captured by a craniocaudal view and a mediolateral oblique view from the same side;
utilizing a symptom identification model to determine whether the plurality of mammogram images have an abnormal state, and generating a plurality of heat maps corresponding to the plurality of mammogram images;
utilizing a false positive filtering model to determine whether the plurality of heat maps have a false positive feature, and generating an abnormal probability corresponding to the plurality of heat maps, wherein the false positive filtering model is trained by a plurality of training images captured by the craniocaudal view and the mediolateral oblique view; and
utilizing a first threshold to determine the abnormal probability, if the abnormal probability is greater than the first threshold, detecting and outputting a lesion position corresponding to the plurality of heat maps.

* * * * *